US008591568B2

(12) United States Patent
Molaei (10) Patent No.: US 8,591,568 B2
(45) Date of Patent: Nov. 26, 2013

(54) MEDICAL DEVICES INCLUDING METALLIC FILMS AND METHODS FOR MAKING SAME

(75) Inventor: Masoud Molaei, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1946 days.

(21) Appl. No.: 11/025,860

(22) Filed: Dec. 29, 2004

(65) Prior Publication Data

US 2005/0197689 A1     Sep. 8, 2005

Related U.S. Application Data

(60) Provisional application No. 60/549,287, filed on Mar. 2, 2004.

(51) Int. Cl.
 *A61F 2/06*         (2013.01)

(52) U.S. Cl.
 USPC ........ 623/1.13; 623/1.42; 623/1.46; 623/1.48

(58) Field of Classification Search
 USPC ........... 623/1.13, 1.15, 1.34, 1.42, 1.44–1.46, 623/1.48, 1.49; 606/191, 194, 195, 198
 See application file for complete search history.

(56) References Cited

U.S. PATENT DOCUMENTS

| | | |
|---|---|---|
| 4,793,348 A | 12/1988 | Palmaz |
| 4,864,824 A | 9/1989 | Gabriel et al. |
| 5,035,706 A | 7/1991 | Giantureo et al. |
| 5,061,914 A | 10/1991 | Busch et al. |
| 5,085,535 A | 2/1992 | Solberg et al. |
| 5,119,555 A | 6/1992 | Johnson |
| 5,245,738 A | 9/1993 | Johnson |
| 5,302,261 A | 4/1994 | LeRoy et al. |
| 5,306,294 A | 4/1994 | Winston et al. |
| 5,325,880 A | 7/1994 | Johnson et al. |
| 5,382,261 A | 1/1995 | Palmaz |
| 5,405,378 A | 4/1995 | Strecker et al. |
| 5,441,515 A | 8/1995 | Khosravi et al. |
| 5,518,680 A | 5/1996 | Cima et al. |
| 5,554,182 A | 9/1996 | Dinh et al. |
| 5,556,413 A | 9/1996 | Lam |
| 5,607,466 A | 3/1997 | Imbert et al. |
| 5,619,177 A | 4/1997 | Johnson et al. |
| 5,656,036 A | 8/1997 | Palmaz |
| 5,667,523 A | 9/1997 | Bynon et al. |

(Continued)

FOREIGN PATENT DOCUMENTS

| | | |
|---|---|---|
| EP | 0472731 | 8/1991 |
| EP | 0 792 627 A2 | 9/1997 |

(Continued)

OTHER PUBLICATIONS

International Search Report for PCT Application No. PCT/US2005/006993.

(Continued)

*Primary Examiner* — Vy Q Bui (74) *Attorney, Agent, or Firm* — Bingham McCutchen LLP (57) ABSTRACT

Medical devices, such as endoprostheses, and methods of making the devices are disclosed. The medical device can include a metallic film comprising nickel, titanium, and chromium, wherein a ratio of a weight of chromium of the metallic film to a combined weight of nickel, titanium, and chromium of the metallic film is at least 0.001. The metallic film can include a shape memory alloy.

10 Claims, 7 Drawing Sheets

(56) References Cited

U.S. PATENT DOCUMENTS

| | | |
|---|---|---|
| 5,674,242 A | 10/1997 | Phan et al. |
| 5,676,697 A | 10/1997 | McDonald |
| 5,728,150 A | 3/1998 | McDonald et al. |
| 5,755,734 A | 5/1998 | Richter et al. |
| 5,800,517 A | 9/1998 | Anderson et al. |
| 5,817,102 A | 10/1998 | Johnson et al. |
| 5,824,042 A | 10/1998 | Lombardi et al. |
| 5,824,049 A | 10/1998 | Ragheb et al. |
| 5,824,054 A | 10/1998 | Khosravi et al. |
| RE35,988 E | 12/1998 | Winston et al. |
| 5,843,158 A | 12/1998 | Lenker et al. |
| 5,843,164 A | 12/1998 | Frantzen et al. |
| 5,843,289 A | 12/1998 | Lee et al. |
| 5,849,206 A | 12/1998 | Amon et al. |
| 5,860,998 A | 1/1999 | Robinson et al. |
| 5,865,723 A | 2/1999 | Love et al. |
| 5,882,444 A | 3/1999 | Flomenblit et al. |
| 5,888,734 A | 3/1999 | Cremer et al. |
| 5,897,911 A | 4/1999 | Loeffler |
| 5,903,099 A | 5/1999 | Johnson et al. |
| 5,941,249 A | 8/1999 | Maynard |
| 5,957,929 A | 9/1999 | Brenneman |
| 5,984,963 A | 11/1999 | Ryan et al. |
| 6,007,573 A | 12/1999 | Wallace et al. |
| 6,015,431 A | 1/2000 | Thornton et al. |
| 6,015,433 A | 1/2000 | Roth |
| 6,017,977 A | 1/2000 | Evans et al. |
| 6,036,725 A | 3/2000 | Avellanet |
| 6,043,451 A | 3/2000 | Julien et al. |
| 6,048,622 A | 4/2000 | Hagood et al. |
| 6,059,766 A | 5/2000 | Greff |
| 6,096,175 A | 8/2000 | Roth |
| 6,099,561 A | 8/2000 | Alt |
| 6,107,004 A | 8/2000 | Donadio, III |
| 6,120,535 A | 9/2000 | McDonald et al. |
| 6,132,460 A | 10/2000 | Thompson |
| 6,133,547 A | 10/2000 | Maynard |
| 6,139,564 A | 10/2000 | Teoh |
| 6,143,022 A | 11/2000 | Shull et al. |
| 6,159,239 A | 12/2000 | Greenhalgh |
| 6,174,330 B1 | 1/2001 | Stinson |
| 6,190,404 B1 | 2/2001 | Palmaz et al. |
| 6,206,911 B1 | 3/2001 | Milo |
| 6,224,627 B1 | 5/2001 | Armstrong et al. |
| 6,224,630 B1 | 5/2001 | Bao et al. |
| 6,245,104 B1 | 6/2001 | Alt |
| 6,254,628 B1 | 7/2001 | Wallace et al. |
| 6,258,117 B1 | 7/2001 | Camrud et al. |
| 6,290,720 B1 | 9/2001 | Khosravi et al. |
| 6,303,100 B1 | 10/2001 | Ricci et al. |
| 6,315,788 B1 | 11/2001 | Roby |
| 6,315,794 B1 | 11/2001 | Richter |
| 6,355,055 B1 | 3/2002 | Waksman et al. |
| 6,379,383 B1 | 4/2002 | Palmaz et al. |
| 6,398,803 B1 | 6/2002 | Layne et al. |
| 6,406,487 B2 | 6/2002 | Brenneman |
| 6,406,490 B1 | 6/2002 | Roth |
| 6,409,749 B1 | 6/2002 | Maynard |
| 6,428,569 B1 | 8/2002 | Brown |
| 6,447,478 B1 | 9/2002 | Maynard |
| 6,454,738 B1 | 9/2002 | Tran et al. |
| 6,458,152 B1 | 10/2002 | Khosravi et al. |
| 6,458,153 B1 | 10/2002 | Bailey et al. |
| 6,471,980 B2 | 10/2002 | Sirhan et al. |
| 6,485,510 B1 | 11/2002 | Camrud et al. |
| 6,506,211 B1 | 1/2003 | Skubitz et al. |
| 6,520,984 B1 | 2/2003 | Garrison et al. |
| 6,527,919 B1 | 3/2003 | Roth |
| 6,533,905 B2 | 3/2003 | Johnson et al. |
| 6,537,310 B1 * | 3/2003 | Palmaz et al. ............ 623/1.13 |
| 6,605,111 B2 | 8/2003 | Bose et al. |
| 6,614,570 B2 | 9/2003 | Johnson et al. |
| 6,618,921 B1 | 9/2003 | Thornton |
| 6,620,192 B1 | 9/2003 | Jalisi |
| 6,620,634 B2 | 9/2003 | Johnson et al. |
| 6,624,730 B2 | 9/2003 | Johnson et al. |
| 6,629,993 B2 | 10/2003 | Voinov |
| 6,632,240 B2 | 10/2003 | Khosravi et al. |
| 6,638,301 B1 | 10/2003 | Chandrasekaran et al. |
| 6,666,882 B1 | 12/2003 | Bose et al. |
| 6,669,719 B2 | 12/2003 | Wallace et al. |
| 6,669,721 B2 | 12/2003 | Bose et al. |
| 6,669,795 B2 | 12/2003 | Johnson et al. |
| 6,673,102 B1 | 1/2004 | Vonesh et al. |
| 6,676,987 B2 | 1/2004 | Zhong et al. |
| 6,695,865 B2 | 2/2004 | Boyle et al. |
| 6,699,278 B2 | 3/2004 | Fischell et al. |
| 6,699,279 B2 | 3/2004 | Stevens et al. |
| 6,746,478 B2 | 6/2004 | Jayaraman |
| 6,752,826 B2 | 6/2004 | Holloway et al. |
| 6,767,418 B1 | 7/2004 | Zhang et al. |
| 6,776,795 B2 | 8/2004 | Pelton |
| 6,820,676 B2 | 11/2004 | Palmaz et al. |
| 6,849,085 B2 | 2/2005 | Marton |
| 6,936,066 B2 | 8/2005 | Palmaz et al. |
| 6,953,560 B1 | 10/2005 | Castro et al. |
| 7,105,018 B1 | 9/2006 | Yip et al. |
| 7,279,175 B2 | 10/2007 | Chen et al. |
| 7,410,497 B2 | 8/2008 | Hastings et al. |
| 7,947,071 B2 | 5/2011 | Schmid et al. |
| 2001/0001834 A1 | 5/2001 | Palmaz et al. |
| 2001/0032013 A1 | 10/2001 | Marton |
| 2001/0039449 A1 | 11/2001 | Johnson et al. |
| 2001/0044647 A1 | 11/2001 | Pinchuk et al. |
| 2002/0007958 A1 | 1/2002 | Rivelli et al. |
| 2002/0017503 A1 | 2/2002 | Banas et al. |
| 2002/0019662 A1 | 2/2002 | Brauckman et al. |
| 2002/0035774 A1 | 3/2002 | Austin |
| 2002/0042645 A1 * | 4/2002 | Shannon .................. 623/1.13 |
| 2002/0046783 A1 | 4/2002 | Johnson et al. |
| 2002/0142119 A1 | 10/2002 | Seward et al. |
| 2002/0151965 A1 | 10/2002 | Roth |
| 2002/0161342 A1 | 10/2002 | Rivelli, Jr. et al. |
| 2002/0162605 A1 | 11/2002 | Horton et al. |
| 2002/0165576 A1 | 11/2002 | Boyle et al. |
| 2002/0165600 A1 | 11/2002 | Banas et al. |
| 2002/0173809 A1 | 11/2002 | Fleischman et al. |
| 2002/0187288 A1 | 12/2002 | Lim et al. |
| 2002/0193869 A1 | 12/2002 | Dang |
| 2002/0195579 A1 | 12/2002 | Johnson |
| 2002/0198584 A1 | 12/2002 | Unsworth et al. |
| 2003/0002994 A1 | 1/2003 | Johnson et al. |
| 2003/0004567 A1 | 1/2003 | Boyle et al. |
| 2003/0018354 A1 | 1/2003 | Roth et al. |
| 2003/0023303 A1 | 1/2003 | Palmaz et al. |
| 2003/0040791 A1 | 2/2003 | Oktay |
| 2003/0050691 A1 | 3/2003 | Shifrin et al. |
| 2003/0059640 A1 | 3/2003 | Marton et al. |
| 2003/0060782 A1 | 3/2003 | Bose et al. |
| 2003/0074049 A1 | 4/2003 | Hoganson et al. |
| 2003/0078649 A1 | 4/2003 | Camrud et al. |
| 2003/0083731 A1 | 5/2003 | Kramer et al. |
| 2003/0127318 A1 | 7/2003 | Johnson et al. |
| 2003/0130718 A1 | 7/2003 | Palmas et al. |
| 2003/0130721 A1 | 7/2003 | Martin et al. |
| 2003/0139797 A1 | 7/2003 | Johnson et al. |
| 2003/0153971 A1 | 8/2003 | Chandrasekaran |
| 2003/0159920 A1 | 8/2003 | Roth |
| 2003/0185895 A1 | 10/2003 | Lanphere et al. |
| 2003/0187495 A1 | 10/2003 | Cully et al. |
| 2003/0212430 A1 | 11/2003 | Bose et al. |
| 2004/0006381 A1 | 1/2004 | Sequin et al. |
| 2004/0014253 A1 | 1/2004 | Gupta et al. |
| 2004/0030377 A1 | 2/2004 | Dubson et al. |
| 2004/0034408 A1 | 2/2004 | Majercak et al. |
| 2004/0054399 A1 | 3/2004 | Roth |
| 2004/0054406 A1 | 3/2004 | Dubson et al. |
| 2004/0059410 A1 | 3/2004 | Cox |
| 2004/0098095 A1 | 5/2004 | Burnside et al. |
| 2004/0107004 A1 | 6/2004 | Levine et al. |
| 2004/0143317 A1 | 7/2004 | Stinson et al. |
| 2004/0199239 A1 | 10/2004 | Austin et al. |
| 2004/0225350 A1 | 11/2004 | Shanley |
| 2004/0254520 A1 | 12/2004 | Porteous et al. |

(56) References Cited

U.S. PATENT DOCUMENTS

| | | | |
|---|---|---|---|
| 2005/0004653 A1 | 1/2005 | Gerberding et al. | |
| 2005/0010275 A1 | 1/2005 | Sahatjian et al. | |
| 2005/0033399 A1 | 2/2005 | Richter | |
| 2005/0165468 A1 | 7/2005 | Marton | |
| 2005/0165469 A1 | 7/2005 | Hogendijk | |
| 2005/0197687 A1* | 9/2005 | Molaei et al. | 623/1.2 |
| 2005/0197690 A1* | 9/2005 | Molaei et al. | 623/1.13 |
| 2006/0069428 A1 | 3/2006 | Feller | |
| 2006/0100659 A1 | 5/2006 | Dinh et al. | |
| 2006/0115514 A1 | 6/2006 | Gengrinovitch | |
| 2006/0122691 A1 | 6/2006 | Richter | |
| 2006/0142838 A1 | 6/2006 | Molaei | |
| 2006/0142842 A1* | 6/2006 | Molaei et al. | 623/1.15 |
| 2006/0142845 A1* | 6/2006 | Molaei et al. | 623/1.22 |
| 2006/0142851 A1* | 6/2006 | Molaei et al. | 623/1.44 |
| 2006/0147492 A1 | 7/2006 | Hunter et al. | |
| 2006/0184231 A1 | 8/2006 | Rucker | |
| 2006/0259131 A1* | 11/2006 | Molaei et al. | 623/1.44 |
| 2006/0271158 A1 | 11/2006 | Olson | |
| 2007/0016283 A1 | 1/2007 | Greenhalgh et al. | |
| 2007/0073385 A1 | 3/2007 | Shaeffer et al. | |
| 2007/0112411 A1 | 5/2007 | Obermiller et al. | |
| 2007/0250156 A1 | 10/2007 | Palmaz | |
| 2008/0027388 A1 | 1/2008 | Banas et al. | |
| 2008/0221665 A1 | 9/2008 | Peckham et al. | |
| 2009/0132022 A1 | 5/2009 | Banas | |
| 2009/0187240 A1 | 7/2009 | Clerc et al. | |
| 2010/0030320 A1 | 2/2010 | Feller, III | |
| 2011/0054590 A1 | 3/2011 | Leopold et al. | |

FOREIGN PATENT DOCUMENTS

| | | |
|---|---|---|
| EP | 1 604 697 | 12/2005 |
| EP | 1 725 186 | 11/2006 |
| EP | 1 725 187 | 11/2006 |
| EP | 1 725 188 | 11/2006 |
| GB | 2 125 442 A | 3/1994 |
| JP | 2003-102849 | 8/2003 |
| JP | 2007/502069 | 9/2007 |
| JP | 2007/526098 | 9/2007 |
| JP | 2007/526099 | 9/2007 |
| WO | WO 96/06814 | 3/1996 |
| WO | WO 98/53362 | 11/1998 |
| WO | WO 99/02092 | 1/1999 |
| WO | WO 99/60267 | 12/1999 |
| WO | WO 99/62432 | 12/1999 |
| WO | WO 00/62711 | 10/2000 |
| WO | WO 01/21097 | 3/2001 |
| WO | WO 01/53559 | 7/2001 |
| WO | WO 01/87371 | 11/2001 |
| WO | WO 01/89420 | 11/2001 |
| WO | 01/95697 | 12/2001 |
| WO | WO 01/91823 | 12/2001 |
| WO | WO 02/34163 | 5/2002 |
| WO | WO 02/38080 | 5/2002 |
| WO | WO 02/38086 | 5/2002 |
| WO | WO 02/060506 | 8/2002 |
| WO | WO 03/003943 | 1/2003 |
| WO | WO 03/011363 | 2/2003 |
| WO | WO 03/013337 | 2/2003 |
| WO | WO 03/015840 | 2/2003 |
| WO | WO 03/018100 | 3/2003 |
| WO | WO 03/075793 | 9/2003 |
| WO | WO 03/075799 A1 | 9/2003 |
| WO | 03/099161 A2 | 12/2003 |
| WO | WO 2004/002370 A1 | 1/2004 |
| WO | WO 2004/008504 | 1/2004 |
| WO | WO 2004/028340 | 4/2004 |
| WO | 2005/084583 | 9/2005 |
| WO | 2005/084584 | 9/2005 |
| WO | 2005/084585 | 9/2005 |
| WO | 2006/125022 | 4/2006 |
| WO | 2006/071215 | 7/2006 |
| WO | 2006/071242 | 7/2006 |
| WO | 2006/071243 | 7/2006 |
| WO | 2006/071244 | 7/2006 |
| WO | 2006/071245 | 7/2006 |

OTHER PUBLICATIONS

International Search Report for PCT Application No. PCT/US2005/007161.

International Search Report for PCT Application No. PCT/US2005/007173.

International Search Report for PCT Application No. PCT/US2005/006895.

International Search Report for PCT Application No. PCT/US2005/007162.

International Search Report from International Application No. PCT/US2005/007282 mailed Jul. 5, 2005, 15 pages.

International Search Report from International Application No. PCT/US2005/007164 mailed Jul. 5, 2005, 13 pages.

International Search Report from International Application No. PCT/US2006/019126 mailed Feb. 1, 2007, 16 pages.

Dieter, George, *Mechanical Metallurgy*, Singapore, McGraw-Hill Book Co., $10^{th}$ Printing 1984, pp. 111-117, 142-145, and 234-237. TA405.D53.

Freiherr, Greg, "Shape-Memory Alloys Offer Untapped", Medical Device & Diagnostic Industry Magazine, Mar. 1998, 5 pages [retrieved on Jun. 30, 2004].

Fu et al., "TiNi-based thin films in MEMS applications: a review", Sensors and Actuators, Article in Press, Elsevier, Feb. 2004, 14 pages.

Gertner et al., "Drug Delivery from Electrochemically Deposited Thin Metal Films", Electrochemical and Sold-State Letter, 6 (4) J4-J6, 2003.

Gertner et al., "Electrochemistry and Medical Devices: Friend or Foe?", The Electrochemical Society Interface, Fall 2003, pp. 20-24.

Gupta et al., "Nitinol Thin Film Three-Dimensional Devices—Fabrication and Applications", http://www.tinialloy.com/pdf/smst.pdf, Sep. 7, 2003 [retrieved Dec. 1, 2004].

He et al., "$CO_2$ laser annealing of sputtering deposited NiTi shape memory thin films", Journal of Micromechanics and Microengineering, May 20, 2004, pp. 950-956.

Kaczmarek, S. M., "Pulsed laser deposition—today and tomorrow", STL'96, Proc. SPIE, vol. 3187, 1997, pp. 129-134.

Krebs et al., "Pulsed Laser Deposition (PLD)—a Versatile Thin Film Technique", Advances in Solid State Physics 2003, 43, 505-517.

Nakayama et al., "Fabrication of micropored elastomeric film-covered stents and acute-phase performances", Journal of Biomedical Mateirals Research Part A, vol. 64A, Issue 1, Sep. 30, 2002, pp. 52-61.

Neocera, Inc. Brochure—Pulsed Laser Deposition, www.neocera.com [retrieved Dec. 1, 2004].

Pelleiter et al., "Effect of high energy argon implantation into NiTi shape memory alloy", Surface and Coatings Technology, 158-159, 2002, pp. 301-308.

Padhi et al., "Planarization of Copper Thin Films by Electropolishing in Phosphoric Acid for ULSI Application", Journal of Electrochemical Society, vol. 150, 2003, pp. G10-G14.

Ren et al., "Carbon nitride materials synthesized by Ion-assisted pulsed laser deposition", Riken Review No. 43, Jan. 2002, pp. 41-44.

Schetky et al., "Issues in the Further Development of Nitinol Properties and Processing for Medical Device Application", Proceedings, ASM Materials & Processes for Medical Devices Conference, Anaheim, in press, 2003, 6 pages.

Shabalovskaya et al., "Comparative performances of Nitinol surfaces in protein adsorption and platelet adhesion—Preliminary results", Institute for Physical Research and Technology, Ames Laboratory, Ames, IA University of Washington, Seattle WA Memry Corporation, Bethel CT, 2004, 10 pages.

Stoeckel et al., "A survey of stent designs", Min Invas Ther & Allied Technol, 11(4), 2002, pp. 137-147.

\* cited by examiner

MEDICAL DEVICES INCLUDING METALLIC FILMS AND METHODS FOR MAKING SAME

RELATED APPLICATIONS

This application claims the benefit of U.S. provisional patent application No. 60/549,287, filed Mar. 2, 2004, which application is incorporated by reference herein.

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis includes a metallic film including an alloy including nickel, titanium, and a strength additive. The film may have a thickness of about 50 µm or less. The strength additive may be chromium.

A ratio of the weight of strength additive to the combined weight of nickel, titanium, and strength additive may be less than 0.0075.

A ratio of the weight of nickel to the combined weight of the nickel, titanium, and strength additive may be at least 0.5 and the ratio of the weight of titanium to the combined weight of the nickel, titanium, and strength additive may be at least 0.44.

A ratio of the combined weight of nickel and titanium to a weight of the metallic film may be at least 0.99. The ratio of the combined weight of nickel and titanium to a weight of the metallic film may be less than 0.998.

A maximum variation in the ratio of the weight of strength additive to the combined weight of nickel, titanium, and strength additive may be less than 20% taken through the thickness of the metallic film. The strength additive may be uniformly distributed throughout the metallic film.

The metallic film may be a tertiary alloy of nickel, titanium, and chromium.

The metallic film may be a vapor deposited film.

The film may include about $5 \times 10^7$ dislocations per $cm^2$ or more.

A thickness of the metallic film may be at least 4 µm, e.g., at least 5 µm. The thickness may be less than 35 µm.

The metallic film may have an extent of at least 5 $mm^2$.

The endoprosthesis may further include a stent. The film and stent may be secured with respect to one another. The film and stent may each include fenestrations. The fenestrations of the film may be smaller than fenestrations of the stent.

In some embodiments, a method of manufacturing an endoprosthesis includes forming a layer by vapor depositing one or more metals on a substrate and irradiating at least some of the deposited metal with particles having an energy of about 50 eV or more.

The deposited metal may include nickel, titanium, and an optional strength additive such as chromium.

The method may include releasing the film from the substrate.

The substrate may be a stent body or a portion thereof.

The depositing may include depositing: (i) nickel from a vapor and (ii) titanium from (a) the same vapor as the nickel or (b) a different vapor.

Irradiating may include irradiating deposited metal with particles having an energy of at least 500 keV.

The depositing and the irradiating may be combined. The particles having an energy of at least 50 eV may include metal ions, e.g., nickel and titanium ions.

In some embodiments, the particles are ions and/or atoms, e.g., ions of a noble gas.

Irradiating may be performed after forming the film.

The layer may have a density N of dislocations per $cm^2$, the density N being at least 100 times larger than a density of dislocations in the absence of irradiating. The density N may be at least $10^{10}$ dislocations per $cm^2$.

The layer may include at least 50 weight percent of nickel and at least 40 weight percent of titanium. The layer may include an amount of strength additive, e.g., chromium. A ratio of a weight of the strength additive of the layer to a combined weight of nickel, titanium, and chromium of the layer may be at least 0.001. The ratio may be 0.01 or less.

The method may include heating deposited metal, e.g., deposited nickel and titanium, to at least 425° C. Heating may be performed after forming the film.

In some embodiments, a method of manufacturing an endoprosthesis includes forming a film by depositing constituents of the film on a substrate. The constituents may include one or more metals, e.g., nickel and titanium. The film has a density N of dislocations per $cm^2$. A density N of dislocations of at least a portion of the film is increased by at least 100 times.

The film may be released from the substrate.

The density N of locations may be increased for at least 20% of the surface area of the deposited metal. The density N of dislocations may be increased for 75% or less of the total surface area.

Increasing the density N of dislocations may be performed before releasing the film from the substrate, if releasing is performed.

Increasing the density N of locations may include striking deposited metal with a plurality of particulates.

Increasing the density N of locations may include irradiating deposited metal with particles having an energy of at least 50 eV.

Increasing the density N of locations may include repeatedly moving at least two different portions of the film with respect to one another.

The method may include heating deposited metal to at least 425° C. The heating may be performed after forming the film.

In some embodiments, a method of manufacturing an endoprosthesis includes depositing a film including one or more metals and having a thickness of at least 4 μm and heating the film by using optical radiation having an intensity sufficient to modify a crystalline structure of the film without rupturing the film. The irradiating the film may anneal the film.

The one or more metals may include nickel and titanium. The depositing may include depositing nickel, titanium, and chromium to provide an alloy comprising nickel, titanium, and chromium.

Irradiating may include irradiating at least 10% of the extent of the film.

Irradiating may be performed without joining another article to the metallic film.

In some embodiments, a method of manufacturing an endoprosthesis includes depositing a film including one or more metals, e.g., nickel and titanium. A topography of the deposited film is smoothed, e.g., by electropolishing.

Other aspects, features, and advantages of the invention will be apparent from the description of the preferred embodiments thereof and from the claims.

BRIEF DESCRIPTION OF THE FIGURES

FIG. 1b is an end-on view of the endoprosthesis in FIG. 1a.

FIG. 3b illustrates a modified microstructure of the deposited metallic film of FIG. 3a.

DETAILED DESCRIPTION

Figure 1A:
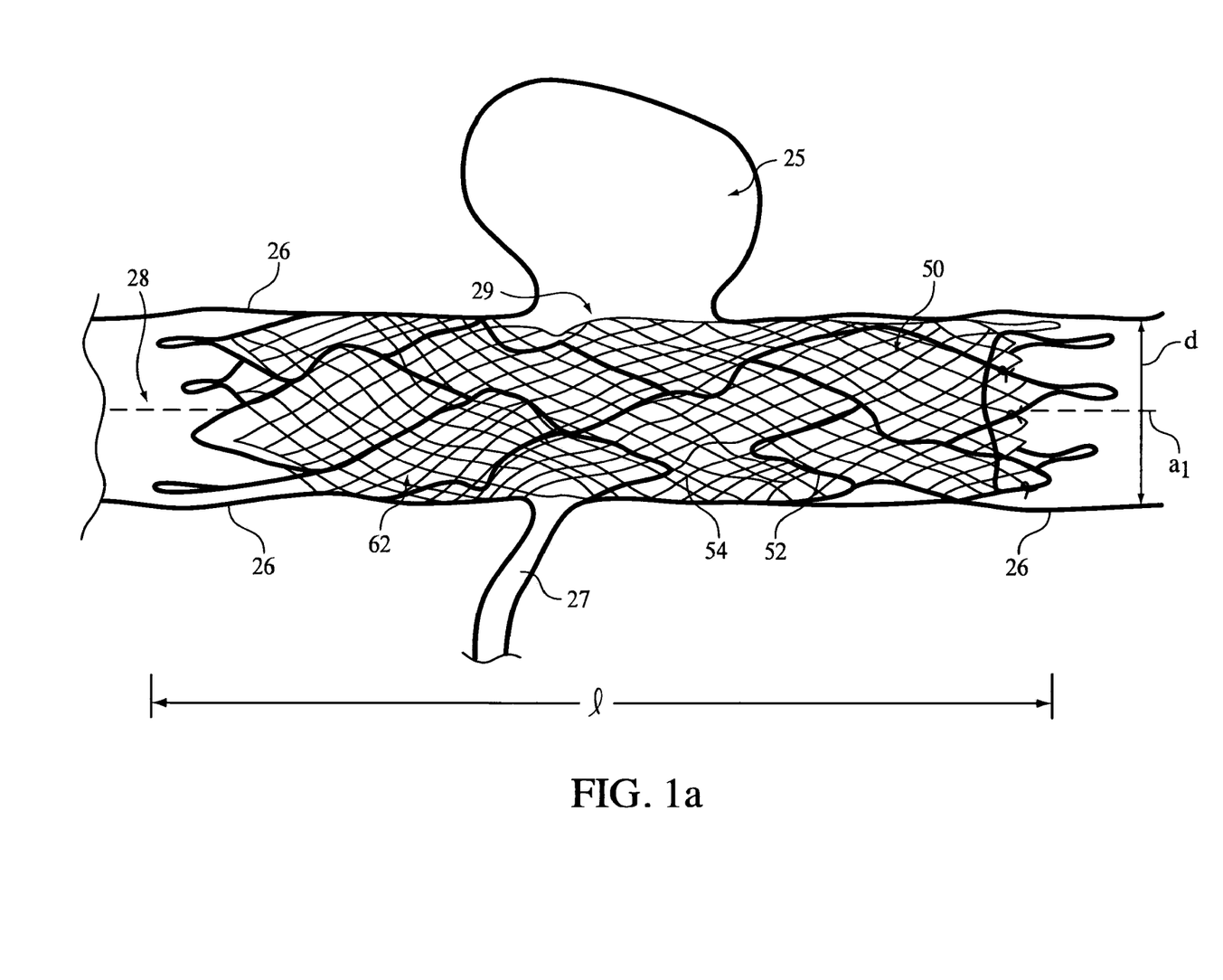
FIG. 1a is a side view of an endoprosthesis in the radially expanded state as deployed within a body passage adjacent an aneurysm.
Figure 1B:
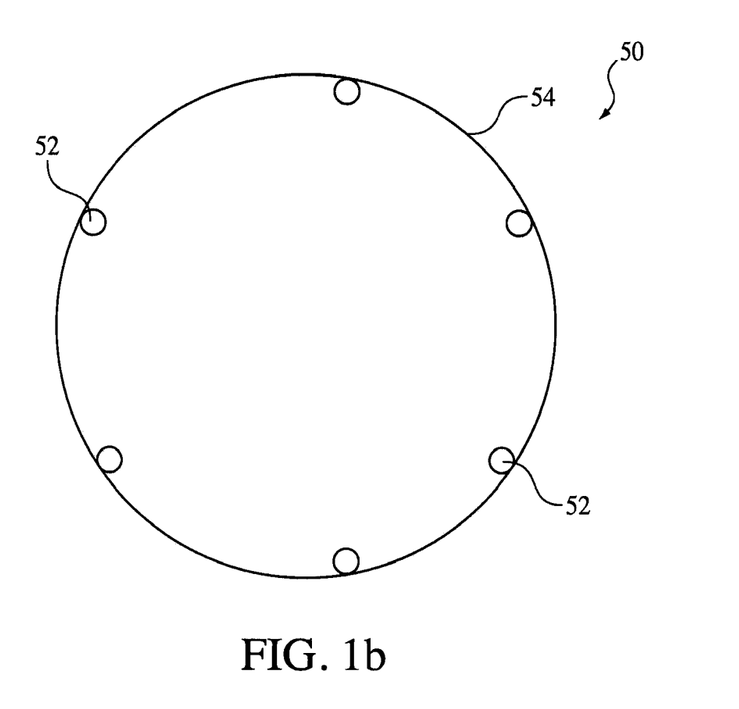

Referring to FIGS. 1a and 1b, an endoprosthesis 50 is deployed within a body passage, e.g., within a blood vessel 26, e.g., in the brain, which is weakened by an aneurysm 25. Endoprosthesis 50 includes a framework, e.g., a stent body 52, covered by a tubular member or cover 54, made of thin metallic film. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover and occlude the fenestrations of the stent.

The endoprosthesis 50 modifies an amount or velocity of blood passing between vessel 26 and aneurysm 25. For example, prosthesis 50 can be deployed to reduce or block blood flow between vessel 26 and aneurysm 25. The endoprosthesis can also reduce blood flow from a feeder vessel 27. If so deployed, prosthesis 50 may sufficiently reduce blood flow to allow clotting or other healing processes to take place within aneurysm 25 and/or opening 29. Tubular member 54 can provide a greater attenuation of the blood flow into the aneurysm 25 than stent body 52 alone. Endoprosthesis 50, however, can allow some flow to pass between vessel 26 and aneurysm 25 even while providing some reduction in the rate and/or volume of flow. Prosthesis 50 can also (or alternatively) allow blood to pass between vessel 26 containing the prosthesis and adjacent vessels, e.g., feeder vessel 27, while still providing reduced flow with respect to the aneurysm.

Figure 2A:
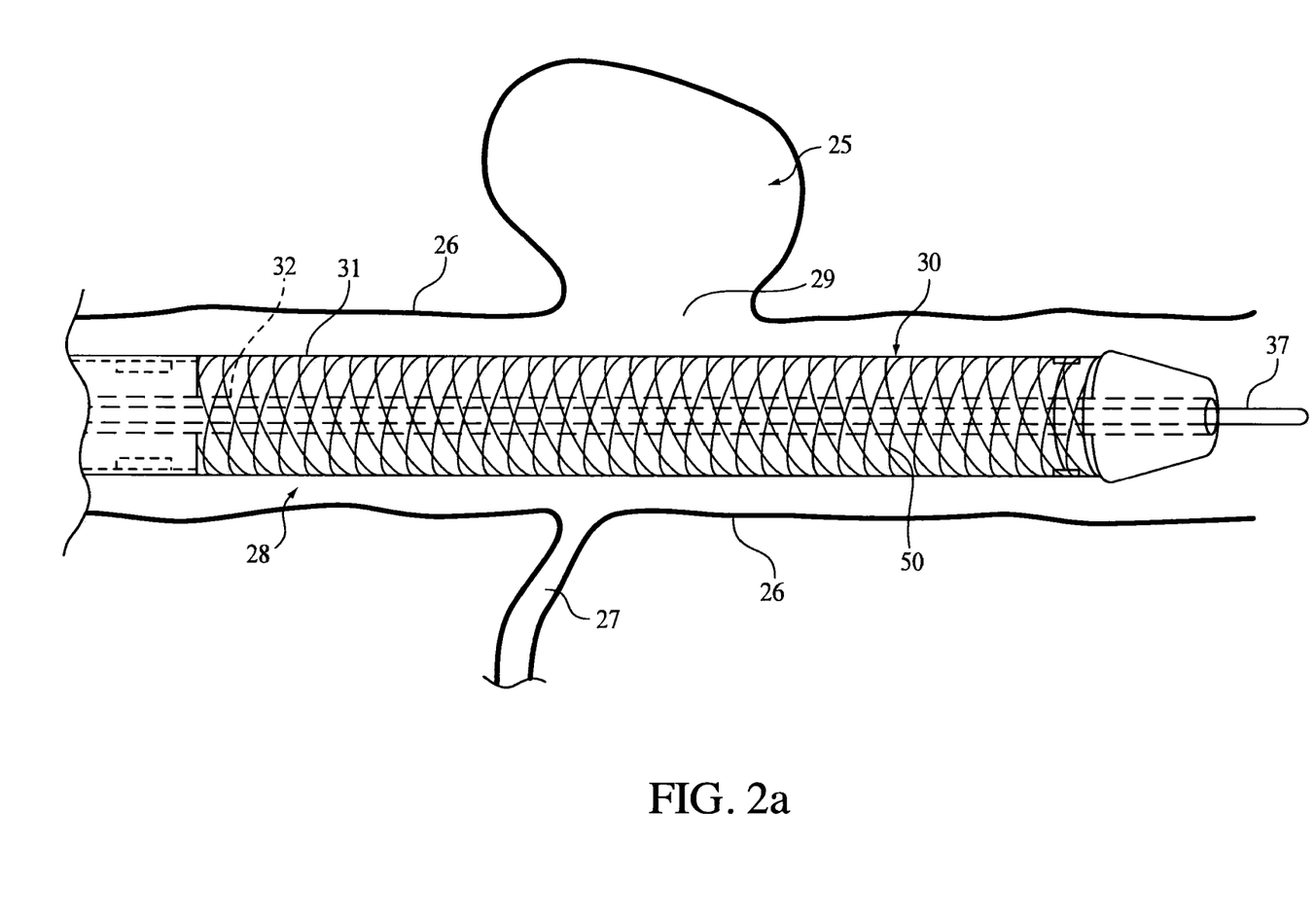
FIG. 2a is a side view of a distal portion of a deployment device prior to radial expansion of the endoprosthesis.
Figure 2B:
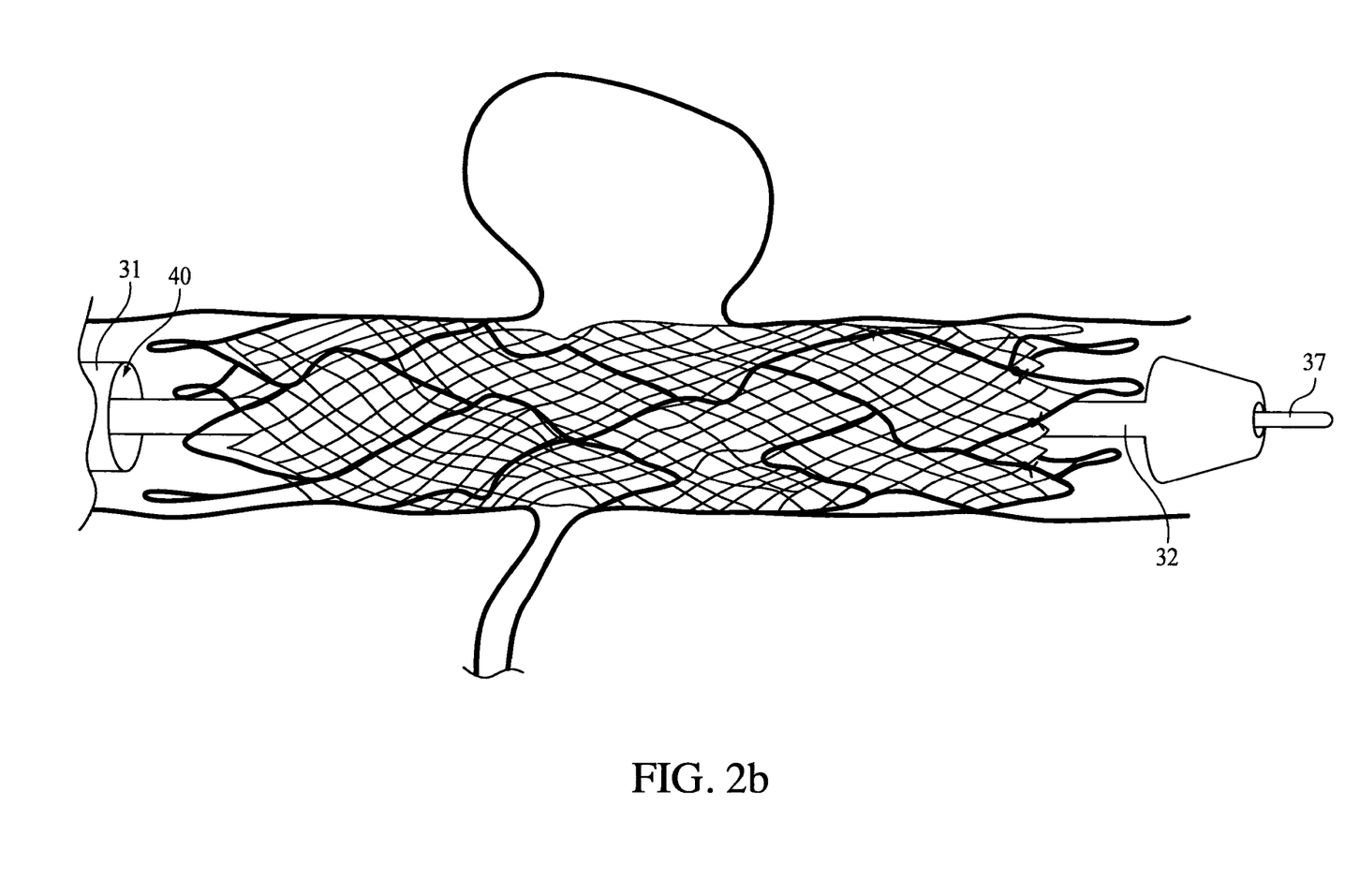
FIG. 2b is a side view of the distal portion of the deployment device subsequent to radial expansion of the endoprosthesis adjacent the aneurysm.

Referring to FIGS. 2a and 2b, endoprosthesis 50 is deployed to aneurysm 25 using a deployment device 30, such as a catheter that can be threaded through a tortuous pathway. The device 30 includes a retractable outer sheath 31 and an inner catheter 32. Device 30 is introduced over a guide wire 37 extending along the interior 28 of vessel 26. During introduction, the endoprosthesis 50 is radially compacted between outer sheath 31 and inner catheter 32 adjacent a distal opening 40 of the outer sheath.

Referring particularly to FIG. 2b, the outer sheath 31 is retracted upon reaching the desired deployment site, e.g., aneurysm 25. In some embodiments, endoprosthesis 50 self-expands by its own internal elastic restoring force when the radially restraining outer sheath is retracted. Alternatively, or in combination with self-expansion, deployment of prosthesis 50 may include use of a balloon or other device to radially expand prosthesis 50 within vessel 26. After deploying the endoprosthesis, the inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

The cover can be fixed to the stent by, e.g. fasteners. Attachment techniques include brazing, welding or attachment with a filament, rivets, or grommets, or crimping, or adhesive. In some embodiments, the tubular member differs from a fabric at least in that the tubular member lacks fibers than can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process. Attachment techniques are described in U.S. patent application Ser. No. 11/025,866, filed contemporaneously herewith and incorporated herein by reference.

The cover is formed of a thin film that exhibits advantageous properties such as strength, toughness, and flexibility by selection of the composition of the film, processing techniques, and mechanical configuration. For example, in particular embodiments, the film is a vapor-deposited material composed of a nickel-titanium alloy having a strength additive, e.g. chromium. The film has a thickness of about 50 μm or less, e.g. about 4-35μ, and includes fine fenestrations which facilitate collapsing the film to small diameter for delivery into the body and expansion at the treatment site, while impeding blood access to the aneurysm. In particular embodiments, the film is processed to modify the number and/or distribution of dislocations, which contribute to strength and toughness of the thin film.

Deposited materials are formed by depositing film constituents from a suspended state, e.g. in a vapor or a vacuum onto a surface. In embodiments, the constituents are suspended, e.g. by bombarding, heating or sputtering a bulk target. The suspended constituents deposit on a substrate to form the film. Deposited films can exhibit highly uniform thickness and microstructure in very thin films, e.g. about 50μ or less, e.g. 4-35μ. Deposition techniques include sputter deposition, pulsed laser deposition, ion beam deposition and plasma deposition. Suitable deposition processes are described in Busch et al. U.S. Pat. No. 5,061,914, Bose et al. U.S. Pat. No. 6,605,111, Johnston U.S. Pat. No. 6,533,905, and Gupta et al. U.S. Ser. No. 2004/0014253, the entire contents of all of which are hereby incorporated by reference.

In particular embodiments, the deposited film is an alloy that includes nickel and titanium, and a strength additive or additives, which modify a mechanical property, e.g., a hardness or elasticity, of the film. In particular embodiments, the film is a tertiary alloy that has substantially no other components besides nickel, titanium, and additive present in an amount greater than 1%, 0.5% or 0.1% or less than 20%, 10%, or 5% by weight of the film. The film may consist essentially of nickel, titanium, and chromium. In embodiments, the deposited film includes between 54 and 57 weight percent nickel with the balance composed essentially of titanium and chromium. In some embodiments, a ratio of a weight of chromium of the film to a combined weight of nickel, titanium, and chromium of the film is at least 0.001, at least 0.002 e.g., at least 0.0025. The ratio of the weight of chromium of the film to the combined weight of chromium, nickel, and titanium of the film can be 0.02 or less, 0.01 or less, e.g., 0.0075 or less. The ratio of the weight of chromium to the combined weight of chromium, nickel, and titanium of the film can be about 0.0025. In embodiments, the alloy exhibits superelastic or pseudo-elastic properties. Superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003.

Figure 3A:
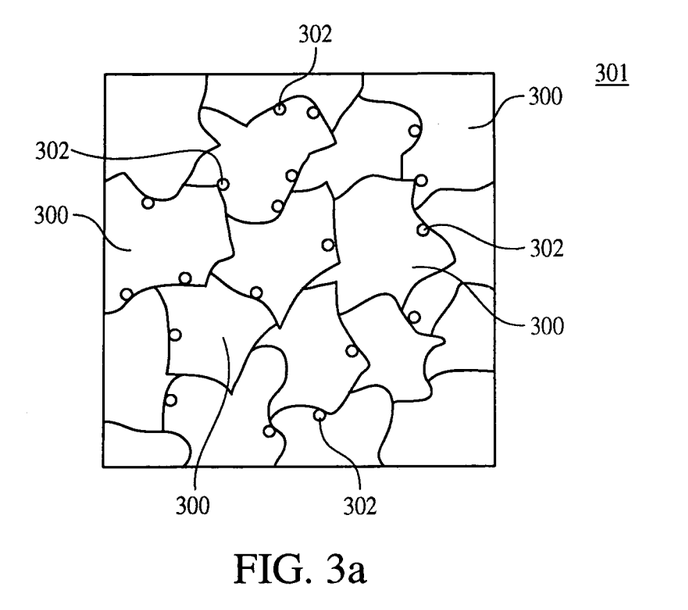
FIG. 3a illustrates a microstructure of a deposited film.

Referring to FIG. 3a, a schematic illustrating the microstructure of a film 301, deposited films may exhibit non-optimal dislocation density. Film 301 includes a plurality of grains 300 and discontinuities, e.g., dislocations 302 which are typically gaps in that grain boundary. Dislocations play a role in the phenomenon of slip, by which metals deform plastically. Increasing dislocation density can harden a metal such as to increase its strength.

Figure 3B:
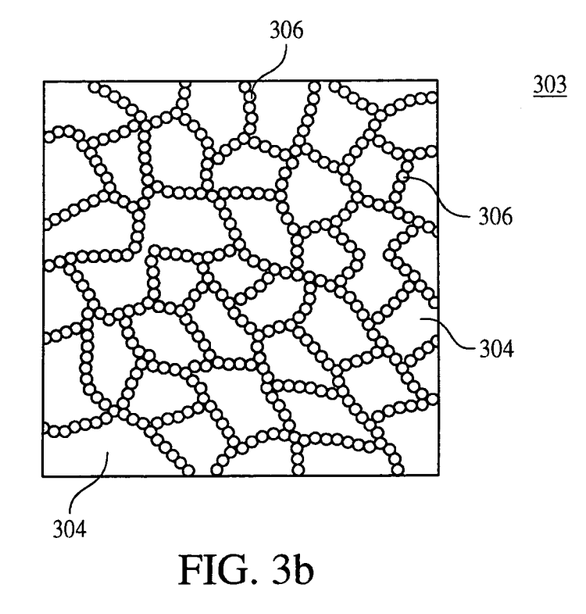

Referring also to 3b, a microstructure of a deposited film 303 that has been subjected to a process that modifies a mechanical property and/or microstructure exhibits a plurality of grains 304 and dislocations 306. Grains 304 of film 303 are smaller and more numerous than grains 302 of film 301. A density per unit area of dislocations 306 of film 303 is substantially greater than a density per unit area of dislocations 302 of film 301. In particular embodiments, the film exhibits a dislocation density of about $5\times10^7$ dislocations/cm$^2$ or more. Dislocations are further discussed by Dieter, Mechanical Metallurgy, International Student Edition, McGraw Hill, 1984, which book is incorporated herein by reference. The occurrence and number density, e.g., density per unit area, of dislocations can be determined by transmission electron microscopy (TEM).

Dislocation density can be modified by imparting energy to the film that effects the microstructure. In embodiments, energy is imparted by striking deposited material with particulates, e.g., as in abrasive blasting. The particulates can include, e.g., metal particulates, silica, alumina, metal oxides, glass, and polymer particulates. The particles may strike the film to deposit enough energy to modify a microstructure without causing gross defects on a scale of microns. In embodiments, the particulates have diameters of 5 μm or less, 2 μm or less, or 1 μm or less. The particulates can have diameters of 25 nm or more, e.g., 50 nm or more.

In some embodiments, energy is imparted by striking deposited material with particles, e.g., atoms, clusters, or ions. The particles can be ions of a noble gas, e.g., argon, krypton, or xenon. Particles can be provided by an ion source, e.g., Kaufman ion sources and Van de Graaff type implanters. A system for irradiating materials with argon ions is disclosed by Pelletier et al., Surface Coatings Technology 158-159, (2002), 301-308, which paper is incorporated herein by reference. In embodiments, the energetic particles having an energy sufficient to, e.g., implant below a surface of deposited material and/or displace deposited material. In particular embodiments, the particles have an energy of at least about 50 eV, e.g., at least 500 eV, at least 1 MeV, e.g., 1.5 MeV or more. The energetic particles can irradiate the substrate and/or deposited material with a current of at least 1 μA cm$^{-2}$, at least 100 μA cm$^{-2}$, e.g., at least 1000 μA cm$^{-2}$. In some embodiments, the substrate and/or deposited material receives a total dose of about $5\times10^{17}$ particles cm$^{-2}$ or less, $1\times10^{17}$ particles cm$^{-2}$ or less, $5\times10^{16}$ particles cm$^{-2}$ or less, e.g., $1\times10^{16}$ particles cm$^{-2}$ or less.

In other embodiments, the film is subject to plastic deformation of deposited material as by cold working, e.g., cold working the released film. In some embodiments, modifying includes repeatedly moving at least two different portions of the film with respect to one another. In some embodiments a mandrel with movable radial projections is used to flex selected portions of the film from its interior or exterior.

Microstructure processing may be performed, e.g., simultaneously, sequentially, or cyclically with repeated deposition. Microstructure processing of deposited material prior to completing the depositing allows deposited material to be modified along its thickness. In some embodiments, the density of dislocations of a deposited film is increased at least 100 times greater, at least 1000 times greater, or at least 10,000 times greater.

In embodiments, different portions of the deposited material have different microstructural properties. The portions of different microstructures can be formed by selectively modifying the microstructure of a deposited film. For example, if the deposited material occupies a total extent, modifying can include modifying 75% or less of the material or 50% or less of the material. At least 25% of the extent of the deposited material, e.g., at least 50% of the extent of the deposited material can be subjected to modifying. In some embodiments, 90% or less, e.g., 60% or less of the extent of deposited material is subjected to modifying. With respect to a thickness of the deposited material, the entire thickness or only portions thereof can be subjected to modifying. For example, at least 25%, at least 50%, or at least 75% of the thickness of deposited material can be subjected to modifying. In embodiments, portions of different microstructures are relative to structural features of film that facilitate operation on a cover. For example, regions of increased dislocation may be provided at regions of increased stress, such as adjacent fenestrations. In embodiments, portions of the film secured to a stent body, as by filaments or fasteners, are subjected to greater stress than portions of the film spaced apart from the secured areas. Portions of the film to be secured to the stent body can be modified while not modifying or modifying to a lesser extent portions spaced apart from the secured portions. For example, portions of the film secured to the stent body and adjacent thereto may have at least 100, at least 1,000, at least 10,000 times more dislocations than more distant portions of the film.

Figure 4:
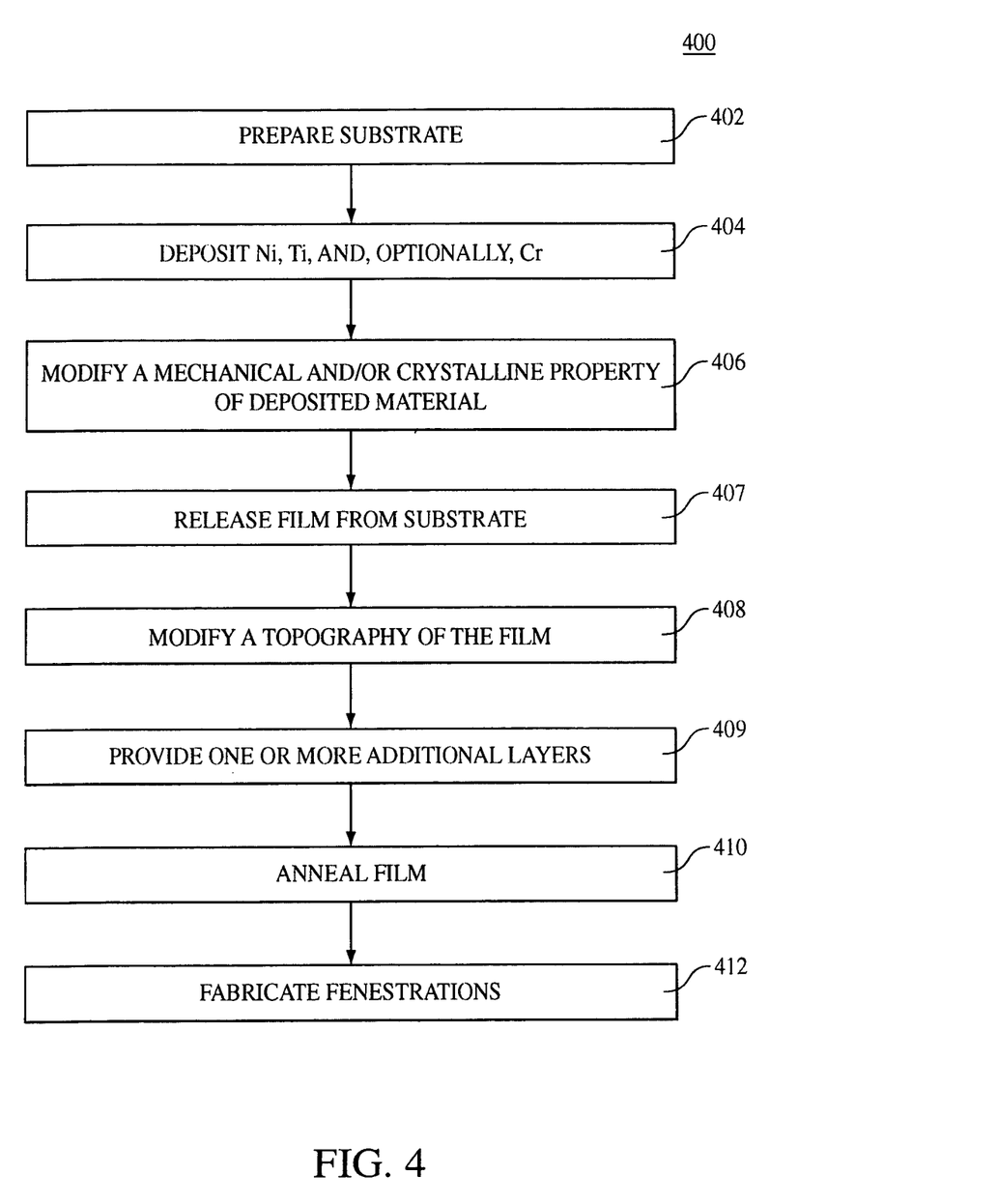
FIG. 4 is a flow chart of an exemplary method for manufacturing an endoprosthesis.

Referring to FIG. 4, in particular embodiments, films exhibiting desirable mechanical and microstructural properties are formed using pulsed laser deposition system. In embodiments, a system 200 includes a laser 202, a vacuum chamber 204 having an optical window 206, a target holder 208, a substrate holder 210, a vacuum pump 212, and a source 214 of gas, e.g., a noble gas such as helium, neon, argon, krypton, or xenon. System 200 also includes a processor 225, which communicates 236 with laser 202, pump 212, gas source 214, and other components of system 200 to provide user control over the operation thereof.

Laser 202 emits a laser beam 216, which is directed by optics 218 through optical window 206 and into vacuum chamber 204. Laser 202 is typically a pulsed laser, e.g., an excimer laser such as a KrF laser, a Nd:YAG laser, or a $CO_2$ laser emitting in the ultraviolet, visible, or infrared. In pulsed laser embodiments, laser 202 typically emits pulses having a full width of 50 ns or less, e.g., about 30 ns or less. Pulse energies are typically at least 0.5 J, at least 2.5 J, at least 5 J, e.g., at least 7.5 J.

Target holder 208 positions a target 220 in a deposition position in which the laser beam 216 impinges upon the target, typically at an angle of 45° with respect to a surface thereof. Optics 218 may focus the laser beam 216 so that the beam impinges upon target 220 with an energy density of at least 0.5 $J\,cm^{-2}$, at least 2.5 $J\,cm^{-2}$, at least 5 $J\,cm^{-2}$, at least 8 $J\,cm^{-2}$, e.g., at least 15 $J\,cm^{-2}$. In some embodiments, target holder 208 positions target 220 less than about 10 cm from a surface of substrate 211. Substrate holder 210 can be configured to maintain substrate 211 at a selected temperature.

Target holder 208 can be configured to position a single target having a desired composition. Alternatively, target holder 220 can be configured to hold more than one target and allow transitioning between the different targets. For example, target 220 can include a first composition, e.g., a nickel-titanium alloy, and a second target 220a can include a second composition, e.g., chromium or other material to be combined with the first composition of target 220. In some embodiments, the other material includes a metal such as iridium. In the following discussion, it is assumed without limitation that target 220 includes a nickel titanium alloy.

Laser beam 216 impinges upon target 220 generating a plume of ejected material including particles, e.g., atoms and ions, and particulates, e.g., solids and/or molten material. For targets used to deposit shape memory films, particles may include nickel ions, nickel atoms, titanium ions, titanium atoms, or combination thereof.

At least some of the ejected material strikes substrate 211. In some embodiments, plume includes at least some particles, e.g., nickel ions and/or titanium ions that have energies sufficient to displace nickel and titanium previously deposited on the substrate. For example, nickel ions and titanium ions of a later ejected plume may be deposited by implantation below a surface of previously deposited nickel and titanium. Such deposition allows the formation of films exhibiting an increased number of dislocations as compared to deposition at lower particle energies. In some embodiments, the nickel ions and titanium ions have energies of at least 75 eV, at least 100 eV, e.g., at least 150 eV. The pressure in chamber 204 is about $10^{-4}$ torr or less, $10^{-5}$ torr or less, $10^{-6}$ torr or less, e.g., about $10^{-7}$ torr or less. In some embodiments, the number of dislocations is at least 100 times greater, at least 1000 times greater, or at least 10,000 greater than in the absence of displacement during deposition. Iridium may be deposited under similar conditions to displace previously deposited nickel and titanium and/or implant the iridium beneath the previously deposited material.

System 200 may include a particle source 230, which can provide particles independent of the target 220 for irradiating substrate 211 and/or upon material from target 220 deposited thereon. In some embodiments, source 230 is an ion source configured to provide a beam 232 of energetic ions 232 such as noble gas ions, e.g., argon ions, krypton ions, or xenon ions or other ions, e.g., nitrogen, or boron.

Energetic particles emitted by particle source 230 can have an energy sufficient to implant below a surface of nickel and titanium deposited on substrate 211. The particles can have enough energy to increase a number of dislocations in the deposited material. In some embodiments, the ions 232 have an energy of at least 50 eV, e.g., at least 500 eV, at least 1 MeV, e.g., 1.5 MeV or more. Ions 232 emitted by source 230 impinge upon substrate 211 and/or upon material from target 220 deposited thereon, with a current of at least 1 $\mu A\,cm^{-2}$, at least 100 $\mu A\,cm^{-2}$, e.g., at least 1000 $\mu A\,cm^{-2}$. In some embodiments, source 230 is used to dose a surface with about $5 \times 10^{17}$ particles $cm^{-2}$ or less, $1 \times 10^{17}$ particles $cm^{-2}$ or less, $5 \times 10^{16}$ particles $cm^{-2}$ or less, e.g., $1 \times 10^{16}$ particles $cm^{-2}$ or less. Irradiation of a deposited material using source 230 can increase the number of dislocations by at least 100 times, at least 1000 times, or at least 10,000 as compared to the absence of such irradiation and the absence of displacement during deposition discussed above.

Source 214 can provide a background pressure of a background gas within chamber 204. In some embodiments, source 214 provides a background pressure of a noble gas that modifies an energy of particles, e.g., atoms and ions, of plume before the particles strike substrate 211 and/or material deposited thereon. In some embodiments, no background pressure is provided. In other embodiments, a background pressure of 1 mbar or less, 0.5 mbar or less, 0.25 mbar or less, e.g., 0.1 mbar or less is provided during the deposition of material from target 220. The background gas can include or consist of argon. In some embodiments, system 200 is configured to reduce the number of particulates that strike substrate 211 as compared to the number of particulates ejected with plume 236. For example, system 200 can include a mechanical filter, e.g., a velocity filter 240 that retards slower moving particulates but allows faster atomic and ionic particles to pass through. Other mechanical filters, e.g., electromagnetic shutters and target spinning can be used. During use of system 200, deposition and irradiation of deposited material may be performed, e.g., simultaneously, sequentially, or cyclically with repeated deposition and irradiation steps. Exemplary ion sources include Kaufman ion sources, e.g., from Kratos Analytical, Inc., New York, N.Y., and Van de Graaff type implanters. A PLD system including an ion source is described in Ren et al., RIKEN Review No. 43 (January, 2002), which paper is incorporated herein by reference. Suitable techniques for reducing the number of particulates are described in, e.g., Chrisey and Hubler, Pulsed Laser Deposition of Thin Films, John Wiley & Sons, New York, 1994, ch. 6, which book is incorporated herein by reference in its entirety. Modifying 406 can be performed before or after releasing 407 the film from the substrate.

Figure 5:
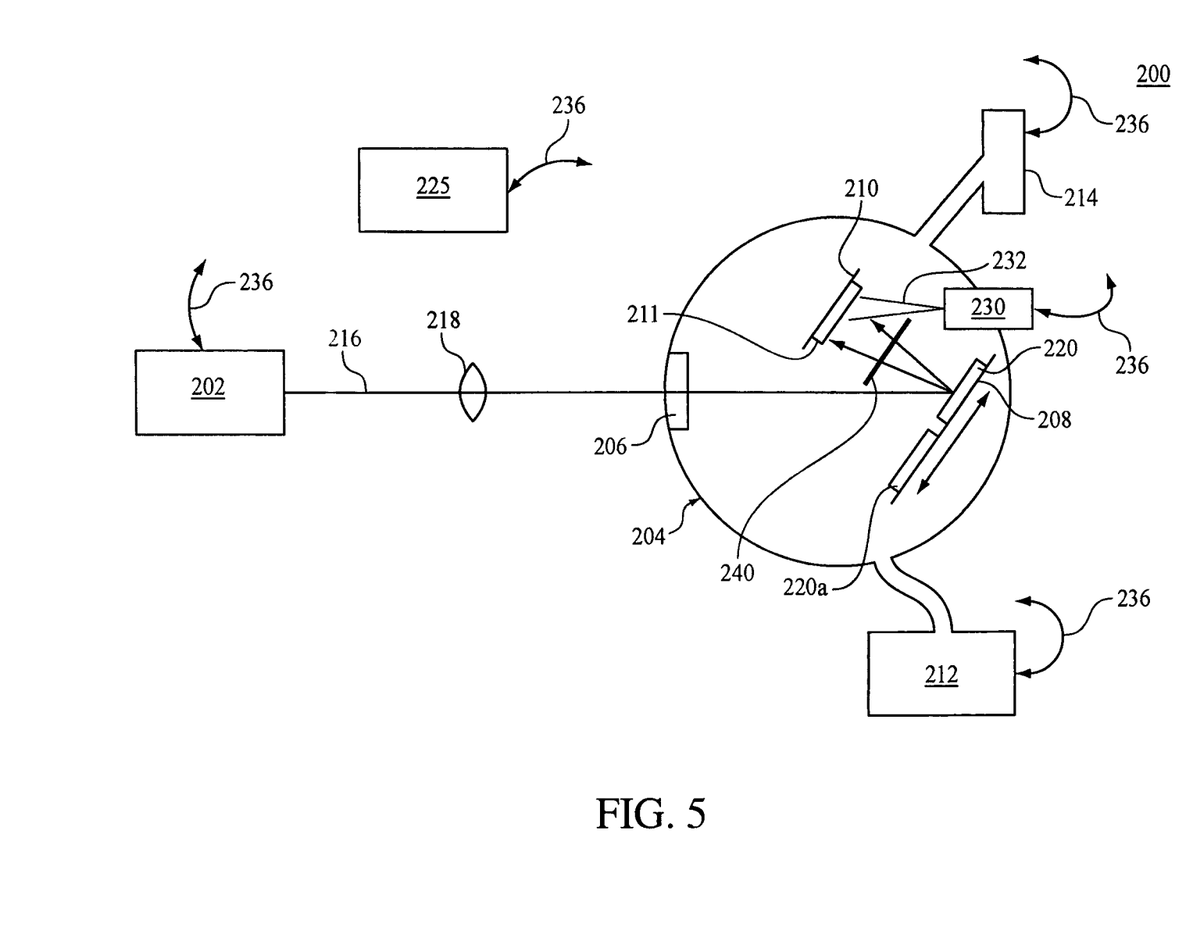
FIG. 5 is a schematic of a pulsed laser deposition system.

Referring to the flow chart of FIG. 5, a method 400 for manufacturing an endoprosthesis includes preparing 402 a substrate, depositing 404 a film, modifying 406 a mechanical property and/or microstructure of deposited material, removing 407 the film from the substrate, modifying 408 a topography of the film, providing 409 one or more additional layers, annealing 410 the film or deposited material, forming 412 fenestrations or other shape features of the film.

Before discussing method 400 further, it is noted that the method is merely exemplary of manufacturing methods. Not all steps shown need be performed. For example, a deposited film can be used without additional layers so that providing 409 additional layers is not performed. Films may be formed by depositing a film on a substrate that itself forms a layer of a film structure so that releasing 407 is not performed. The order of steps may be altered or performed concurrently. Several steps may be combined into one step. Other steps may also be performed.

Turning to method 400, preparing 402 the substrate can include providing a substrate suitable for receiving deposited material from a vapor. Exemplary substrate materials include silicon wafers, glass, quartz, metals, such as aluminum, nitinol, or chromium, and polymers, such as polyimide resins.

The substrate can be two-dimensional, e.g., planar, or three-dimensional, e.g., cylindrical, conical, spherical, or combination thereof. Films deposited as generally two-dimensional may be shaped to have a three-dimensional extent, e.g., a tube-like extent as tubular member 54. For example, a three-dimensional tube-like extent may be achieved by rolling a film about an axis, e.g., parallel to one of its edges or its length. A portion of the rolled film may be overlapped and secured together. The two-dimensional film may be deposited with essentially any shape, e.g., circular, triangular, rectangular, and other polygonal shapes A film or thin film having a three-dimensional extent can be prepared by depositing first and second layers comprising nickel, titanium, and, optionally, chromium. The first and second layers are spaced apart by a sacrificial layer comprising, e.g., a deposited metal that can be etched away without substantial etching of the first and second layers. In some embodiments, the sacrificial layer is chromium. The sacrificial layer is etched away leaving a space between the first and second layers. A mandrel can be used to spread the first and second layers further apart, e.g., to form a tube-like structure.

As an alternative to or in combination with shaping a two-dimensional film or thin film structure, a film or thin film structure with three-dimensional extent can be obtained by depositing material on a substrate itself having a three-dimensional extent. For example, the substrate can be an endoprosthesis or portion thereof, e.g., a stent body. Material deposited upon such a substrate forms a layer on the substrate. In such embodiments, at least some of the deposited material is not released 407 from the substrate. Thus, method 400 need not include releasing step 408.

Films and thin film structures can have three-dimensional extents other than tubular, e.g., cylindrical, conical, basket-shaped, or spherical. An end of the three-dimensional structure may be closed. Whether manufactured as an initially two- or three-dimensional structure, the film or thin film structure can be secured to a substrate or other structure, e.g., a stent body, to provide an endoprosthesis including a metallic film. Preparing 402 the substrate may include subjecting the substrate to ion bombardment or other cleaning technique to improve adhesion of subsequently deposited material.

In some embodiments, the substrate includes a sacrificial layer to facilitate removal 407 of deposited material. For example, the substrate can include a silicon surface coated with a sacrificial chromium layer. Material of the film, e.g., nickel, titanium, and, optionally, chromium, are deposited on the sacrificial layer. Once deposition 404 is completed, the film can be released 407 from the sacrificial layer using, for example, an acid etch. Preparing 402 the substrate may include patterning a sacrificial layer, e.g., a photo resist, on the substrate so that some of the deposited material can be removed. For example, the pattern of photo resist may correspond to a plurality of fenestrations to be formed in the resulting film or layer. Alternatively, selected portions of the deposited material may be removed after deposition 404. Removal of selected portions of material can be performed using photolithographic patterning of a photo resist followed by chemical etching. Laser cutting may be used to remove selected portions of material.

In some embodiments, a substrate receiving deposited material is maintained at a selected temperature during a portion or all of deposition. In some embodiments, the temperature is insufficient to crystallize nickel and titanium deposited onto the substrate during a portion or all of deposition. For example, the temperature of the substrate can be maintained, during a portion or all of deposition, at less than 350° C., at less than 250° C., at less than 100° C., at less than 0° C., or at less than −75° C. In some embodiments, the temperature of the substrate is sufficient to anneal 410, e.g., crystallize, deposited nickel and titanium. For example, the temperature of the substrate can be maintained, during a portion or all of deposition, at 250° C. or higher, at 400° C. or higher, or at 500° C. or higher. Annealing 410, however, can be performed by heating the film, e.g., heating to 500° C. or higher, after releasing 407 the film from the substrate. In any event, annealing 410 can be performed in an inert atmosphere, e.g., in the absence of oxygen and/or nitrogen, or a vacuum, e.g., about $10^{-6}$ torr or less.

Depositing the film 404 typically includes subjecting one or more targets to an excitation process that produces a vapor of target material such as by using, e.g., physical vapor deposition, sputter deposition, pulsed laser deposition (PLD), ion beam deposition, plasma deposition and the like. The vapor from the target(s) deposits on the substrate with increasing thickness to form a film. The one or more targets are typically metal targets that have a composition related to that of the desired film. For example, in some embodiments, at least one target includes a combination of nickel and titanium and a second target includes chromium. By depositing vapor from both of these targets, a film including nickel, titanium, and chromium can be obtained. A single target including Ni, Ti, and Cr can also be used. In some embodiments, the composition of the one or more targets is not identical to the desired composition of the film. For example, the target may be enriched in one of nickel or titanium relative to the other to compensate for a reduced tendency of the enriched metal to enter the vapor or deposit on the substrate.

In some embodiments, chromium is deposited so that a maximum relative variation, with respect to a thickness of the deposited film, of a ratio of the weight of chromium to a combined weight of nickel, titanium, and chromium is 0.25 or less, 0.1 or less, e.g., 0.05 or less. For example, for chromium present in an average amount of 0.5 weight percent, the chromium concentration might vary between 0.45 and 0.55 weight percent. In some embodiments, a maximum relative difference between (a) the ratio of the weight of chromium at a first depth or first depth range to a combined weight of nickel, titanium, and chromium at the first depth or first depth range and (b) the ratio of the weight of chromium at a second depth or second depth range to a combined weight of nickel, titanium, and chromium at the second depth or second depth range may be less than 0.25, less than 0.15, e.g., less than 0.05. The first depth range can be disposed adjacent a surface of the film, e.g., between 0 and 1 μm deep and the second depth range is disposed within the film, e.g., at least 2.5 microns from the surface of the deposited film.

In some embodiments, the film is deposited over an extent of at least 5 mm$^2$, e.g., at least 25 mm$^2$. The extent of the film is the area occupied by the film including the area of any fenestrations or other apertures. For example, a film having a width of 1 mm and a length of 10 mm would have an extent (w×1) of 10 mm$^2$ whether or not the film included any fenestrations. An extent of a cylindrical film can be determined by the product h×d×π, where h is the height of the cylindrical film and d is the diameter of the cylindrical film. An extent of films having other geometries can be determined in similar fashion. Fenestrations or other apertures do reduce a surface area of film itself (but not the extent) whether in two or three dimensions.

In some embodiments, the width of the deposited film is at least 4500 μm, at least 9000 μm, or at least 18,000 μm. The width w can be less 30,000 μm, less than 24,000 μm, or less than 15,000 μm. When configured as a cylinder (as seen for tubular member 54), diameter d can be at least 1400 μm, at least 2850 μm, or at least 5,700 μm. Diameter d can be less than 10,000 μm, less than 7,500 μm, or less than 5,000 μm.

In some embodiments, the length of the film is at least 5 mm, at least 10 mm, at least 20 mm, or at least 30 mm. When configured as a cylinder, height h may be the same as the length.

In some embodiments, a film is used without additional layers to form a tubular member. In other embodiments, one or more additional layers is provided 409. Each of the one or more additional layers may be discontinuous or continuous with respect to the deposited film. The additional layers may include a biocompatible material, such as a polymer, carbon, a salt, a polysaccharide, a metal, e.g., gold, iridium, or platinum, or a metallic oxide, e.g., iridium oxide ($IrO_x$). Oxide layers, e.g., $IrO_x$, can be formed by reactive magnetron sputtering of iridium in an oxygen atmosphere or pulsed laser deposition using an iridium target in an oxygen atmosphere. Suitable coatings are described in U.S. Pat. Nos. 6,245,104; 6,099,561; and 6,387,121.

Exemplary polymer layers can be provided 409 by, e.g., spin coating, dip coating, spray coating, or sputtering. Suitable polymers include, e.g., biocompatible, non-porous or semi-porous polymer matrices made of a fluoropolymer, e.g., polytetrafluoroethylene (PTFE) or expanded PTFE, polyethylene, natural nylon, a butyric acid derivative, e.g., poly-4-hydroxybutyrate, poly-4-hydroxybutyrate, or poly-(3-hydroxybutyrate-co-4-hydroxybutyrate), aqueous acrylic, silicone, polyester, polylactic acid, polyamino acid, polyorthoester, polyphosphate ester, polypropylene, polyester, or combinations thereof. In some embodiments, the layer includes a urethane alone or in combination with one or more additional polymers. Exemplary urethanes include, e.g., polyurethane/silicon copolymers, polyurethane, and dispersions and/or emulsions including urethane.

In some embodiments, the layer includes a polymer configured to release a therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

A total thickness of a layer structure is given by the sum of the thicknesses of the deposited film and any additional layers. In some embodiments, total thickness is at least 7.5 μm, at least 15 μm, or at least 25 μm. In some embodiments, total thickness is 250 μm or less, 125 μm or less, 75 μm or less, 50 μm or less, 35 μm or less, e.g., 25 μm or less. The thickness of additional layers, if present, may be less than that of the deposited film. For example, a ratio of the sum of the thicknesses of the additional layers to the total thickness may be 50% or less, 25% or less, 10% or less, 5% or less, e.g., 1% or less. In some embodiments, the total thickness equals a thickness of the deposited film.

In some embodiments, the deposited film or an additional layer includes a plurality of pores having a size suitable to facilitate adhesion of cells thereto. In some embodiments, the pores are 25 μm deep or less, 10 μm deep or less, e.g., 5 μm deep or less. A width of the pores may be 50 μm or less, 25 μm or less, e.g., 10 μm or less. Pores can be formed by photolithography of an $IrO_x$ layer.

In some embodiments, a thin film structure includes a sandwich of layers. For example, the thin film structure can include first and second metallic thin films spaced apart by a spacer layer. A thin film structure can include first and second layers spaced apart by a metallic film.

Annealing 410 the film or deposited material typically includes heating the material to at least 500° C. Annealing 410 can be performed after releasing 412 the film from the substrate, if releasing is performed. Annealing 410 can be performed before providing 409 one or more additional layers.

In some embodiments, annealing 410 includes heating the film by using optical radiation having an intensity sufficient to modify a crystalline structure of the film without rupturing the film. For example, the film may be irradiated with laser light, e.g., laser pulses from a $CO_2$ laser.

The irradiation may be performed without joining another article, e.g., another film or stent body, to the film. For example, the irradiation may exclude laser welding of the film. Techniques for annealing via irradiating are discussed in He at al., J. Micromech. Microeng., 14 (2004) 950-956, which paper is incorporated herein by reference. Annealing 410 may include irradiating at least at least 10%, e.g., at least 205 of the extent of the film. The irradiating may be performed in a geometric pattern related to the presence of fenestrations or other shape features of the film.

In some embodiments, the film is subjected to process 408 in which the topography of the film can be smoothed, such as by reducing or removing the presence of sharp edges or projections. For example, the film can be polished using a plurality of particulates via a dry polishing process or a slurry polishing process in which the particles are entrained by a fluid, which may be a liquid, such as water or an aqueous solution. The particulates may include, e.g., silica, fumed silica, alumina, fumed alumina, colloids such as colloidal silica and/or colloidal alumina, ferric oxide powder, or polycrystalline diamond particulates. The particulates may have diameters of about 1 μm or less, 0.3 μm or less, or 0.1 μm or less. Such particulates are available from, e.g., Lapmaster International, Morton Grove, Ill. and MIPOX International Corporation, Hayward, Calif. In some embodiments process 408 smoothes the topography of the film and includes abrasive polishing, such as by abrasive blasting, e.g., bead blasting. The particulates may be entrained in a low-pressure fluid, e.g., a gas, having a pressure of, e.g., about 5 pounds per square inch (psi) or less, 2 psi or less, or 1 psi or less. The particulates may have sizes and compositions as discussed above.

In some embodiments, the process 408 smoothes the topography of the film and includes electropolishing the film. Electropolishing typically includes contacting the film with an electrolyte solution such as, e.g., an acid, which can include, e.g., sulfuric acid, phosphoric acid, nitric acid, oxalic acid, or combination thereof. In some embodiments, the acid concentration is reduced by at least 5%, at least 10%, e.g., at least 20% as compared to an acid concentration used for a part having a minimum thickness of at least 250 μm or more. The film and electrolyte can be subjected to a relative velocity difference, e.g., by rotating the film and/or by flowing the electrolyte in a typically laminar fashion over the film.

A counter electrode and a reference electrode, such as a saturated calomel electrode, are also placed in electrical communication with the electrolyte. A potential difference is created between the counter electrode and the film. Typically, the potential is arranged such that the film is oxidized thereby acting as an anode and the counter electrode is reduced thereby acting as a cathode. The reference electrode is used to monitor the potential difference. A current measuring device monitors current passing between the film and counter electrode.

Upon the application of an initial potential difference between the film and counter electrode, an initial current passes therebetween and dissolution of film material typically occurs at sites having higher surface energies, such as grain boundaries and other crystallographic features. As the potential difference is increased, the current passing between the film and counter electrode first increases and then becomes insensitive to further increases in the potential difference. In the insensitive potential difference regime, in which a plot of current v. potential difference may have a negligible slope, further dissolution of the film is limited by mass transport through a boundary layer adjacent the film and the bulk electrolyte solution. Microscopic features such as projections and other high points of the film closer to the bulk solution dissolve faster than macroscopic portions, e.g., flat portions, of the film more distant from the bulk solution. The potential difference regime at which such dissolution occurs is determined by the electropolishing conditions including the electrolyte, the electrolyte concentration, the temperature, the diffusion coefficient of dissolved species and the electrolyte, the temperature, and the hydraulic conditions, e.g., the relative velocity difference between the film and the bulk solution. Still further increases in the potential difference between the counter electrode and film may cause the current between the film and counter electrode to increase and be accompanied by other processes such as oxygen evolution.

In some embodiments, electropolishing is performed under conditions in which a plot of current v. potential difference has a negligible slope. Electropolishing can be performed under galvanostatic conditions in which a constant current passes between the film and the counter electrode. The potential difference as determined by the reference electrode, e.g., by a SCE reference electrode, may be about 2000 $mV_{SCE}$ or less, 1000 $mV_{SCE}$ or less, 500 $mV_{SCE}$ or less, or 250 $mV_{SCE}$ or less. The current density between the film and the working electrode is typically about 1 A cm$^{-2}$ or less, 10 mA cm$^{-2}$ or less, 1 mA cm$^{-2}$ or less, 500 μA cm$^{-2}$ or less, 100 μA cm$^{-2}$ or less, or 50 μA cm$^{-2}$ or less. An amount of material removed from the film relative to the thickness of the film may be 10 μm or less, 5 μm or less, 2 μm or less, 1 μm or less, or 0.5 μm or less. In some embodiments, the electropolishing process is monitored by monitoring the total amount of current passed through the film.

In some embodiments, the process that smoothes the topography of the film does not substantially smooth the topography of the film itself but coats the film with one or more layers, e.g., a polymer layer. Hence, process 408 and providing 409 an additional layer may be the same process. Compared to the untreated film, the one or more layers can have a smoother topography, an increased lubricity, a lower surface energy, lower surface area or combination thereof. For example, a film comprising the layer may exhibit a lower coefficient of friction when translated against the inner surface of a sheath used to deploy a prosthesis including the film. Exemplary techniques for applying the layer include dip coating, spray coating, and spin coating.

In some embodiments, an added layer partially or completely occludes fenestrations of the deposited film by an amount sufficient to limit or prevent fluid, e.g., blood, from passing therethrough.

In embodiments, alloys other than Ni—Ti—Cr can be processed by mechanical and/or crystalline property modification. For example, the deposited film can include an alloy of nickel and titanium present in amounts sufficient to provide the deposited film with desirable mechanical or shape memory properties. The deposited film can be a binary alloy having no other components besides nickel and titanium present in an amount greater than 1% by weight of the film, no other components besides nickel and titanium present in an amount greater than 0.5% by weight of the film, e.g., no other components besides nickel and titanium present in an amount greater than 0.2% by weight of the film. The film may consist essentially of nickel and titanium.

In embodiments, the alloy has a martensite start temperature that is at least as high as, e.g., higher than, a human body temperature. For example, in some embodiments, one or both of the stent body and tubular member do not complete a transition to the austenitic phase when implanted in a human. The martensite start temperature may be selected close to 37° C. to maximize a radial force exerted by the prosthesis without beginning the transition. The martensite start temperature may be 37.25° C. or greater, 38° C. or greater, 39° C. or greater, 40° C. or greater, e.g., 42.5° C. or greater. The martensite start temperature may be 45° C. or less, 42.5° C. or less, 40° C. or less, 39° C. or less, 38° C. or less, e.g., 37.5° C. or less. In some embodiments, the prosthesis requires expansion by a balloon or other expandable device. Alternatively, the prosthesis may be self expanding. In some embodiments, at least one of the stent body 52 and tubular member has an austenite finish temperature that is at least as low as, e.g., lower than, a human body temperature. The austenite finish temperature may be 37° C. or less, 36° C. or less, 35° C. or less, e.g., 34° C. or less. The austenite finish temperature may be 0° C. or more, 15° C. or more, e.g., 26° C. or more. In other embodiments, the deposited film is an alloy such as stainless steel or a pure metal, e.g. titanium.

Referring back to FIGS. 1*a* and 1*b*, an exemplary endoprosthesis 50 is discussed further.

In embodiments, depending upon the application, prosthesis 50 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 50 can have a length along axis $a_1$ of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

Figure 6:
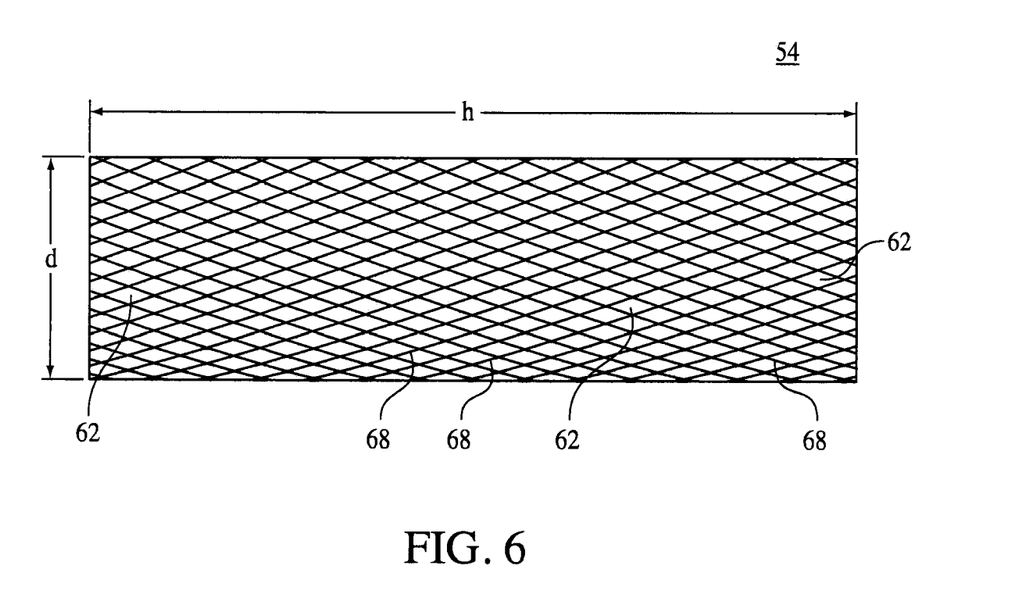
FIG. 6 is a side view of the tubular member of FIG. 1a but removed from the endoprosthesis.

Referring to FIG. 6, in which tubular member 54 is shown with stent body 52 removed, tubular member 54 is defined by a plurality of longitudinal members 68, which themselves define fenestrations 62 therebetween. Fenestrations 60,62 are shown as diamond-shaped but may have different shapes, e.g., circular, oval, or cross-shaped. Unless otherwise specified, the term "longitudinal" when used with the longitudinal members of the stent body and tubular member, does not require that these members extend along a longitudinal dimension of the prosthesis.

In some embodiments, the fenestrations 62 are asymmetric having a short axis of between about 25 and 500 µm, e.g., between about 150 and 300 µm and a long axis of between about 50 and 1500 µm, e.g., between about 600 and 1000 µm. The fenestrations may have an area of at least about 2,500 µm$^2$, e.g., at least about 5,000 µm$^2$. The fenestrations may have an area of about 5×105 µm$^2$ or less, e.g., about 2.5×105 µm$^2$ or less.

Tubular member 54 can include fewer fenestrations than shown or none at all. In some embodiments, the fenestrations occupy at least 50%, at least 70%, at least 80%, at least 90%, at least 95%, at least 97.5%, e.g., at least 98% of an area of the tubular member. The fenestrations can occupy 70% or less, 50% or less, 30% or less, 20% or less, 10% or less, e.g., at least 5% or less of the area of the tubular member. The tubular member may include a first portion, e.g., a central portion, in which fenestrations occupy a first amount of the area and a second portion, e.g., one or both end portions, in which fenestrations occupy a second, optionally smaller, amount of the area. Individual fenestrations of a tubular member occupy about 35% or less, 25% or less, 10% or less, 5%, e.g., 2.5% or less of a length, width, or circumferential dimension of the tubular member, although tubular members may have larger fenestrations.

Longitudinal members 68 of tubular member 54 define a cross-sectional area of between about 45 µm$^2$ and about 1000 µm$^2$. In some embodiments, longitudinal members 68 have a thickness of between about 5 µm and 20 µm and a width of between about 15 µm and 50 µm.

In some embodiments, all or a portion of tubular member 54 can be positioned external to stent body 52. All or a remaining portion of tubular member 54 can be positioned internal to stent body 52. Stent body 52 and tubular member 54 may have mismatched diameters. In some embodiments, such as, e.g., when tubular member 54 surrounds stent body 52, stent body 52 has a larger diameter than tubular member 54. In such embodiments, the diameter of the stent body 52 is the diameter to which stent body 52 would expand in the absence of tubular member 54. A ratio of the diameter of tubular member 54 to the diameter of stent body 52 in the absence of tubular member 54 may be about 0.9 or less, about 0.85 or less, or about 0.8 or less. Thus, stent body 52 may subject tubular member 54 to an outward radial force even after deployment within a body passage.

At least one of stent body 52 and tubular member 54 can be formed of an elastic material, e.g., nitinol, that can be reversibly compacted and expanded, e.g., elastically or through a material phase transition. Upon expansion, prosthesis 50 may exert an outward radial force sufficient to retain the prosthesis in the deployed position with respect to the body passage. Tubular member 54 may, but does not necessarily, contribute a significant portion of the outward radial force. For example, at least 50%, at least 75%, at least 90%, or at least 95% of the outward radial force can be exerted by stent body 52. In some embodiments, all of the outward radial force is exerted by stent body 52.

In some embodiments, at least one of the tubular member and stent body are shape set at a selected diameter or shape, which need not be the same. The tubular member can be shape set to have a selected diameter or shape that reduces a stress of the tubular member when deployed within a body passage. For example, the tubular member can be shape set at a diameter equal to or less than the diameter to which stent body 52 would expand in the absence of the tubular member. A ratio of the shape set diameter of tubular member 54 to the expanded diameter of stent body 52 in the absence of tubular member 54 may be about 1 or less, about 0.95 or less, or about 0.9 or less. The tubular member can be shape set at a diameter about the same as or larger than an inner diameter of a delivery device sheath that surrounds the tubular member during implantation.

In other embodiments, a deposited thin film is useable as an endoprosthesis without a supporting stent. For example, a deposited thin film formed of a selected alloy and/or microstructure modification to enhance strength. In embodiments, the endoprosthesis is a tube of substantially uniform thickness. In other embodiments, the thin-film endoprosthesis can include a pattern of integral reinforcement regions like stent struts where the film is thicker, with thin regions between the reinforcement regions including fenestrations. For example, in embodiments, the reinforcement regions have a thickness of 20-50µ and the thinner regions about 2-20µ. The thin film is formed of an alloy of Ni—Ti—Cr.

In the embodiment shown, endoprosthesis 50 has a generally tubular shape. In some embodiments, however, the endoprosthesis (or stent body 52 or tubular member 54 individually) has or includes other shapes such as conical, oblate, and branched. The endoprosthesis may have a closed end to form, e.g., a basket shape. Thin films, discussed above, composed of Ni—Ti-strength additive alloys and/or with modified microstructures, can be used in other applications. Examples include baskets, filters, catheters, guidewires, and medical balloons, such as an angioplasty balloon.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application Ser. No. 11/025,464, and filed concurrently herewith, which application is incorporated herein by reference.

An endoprosthesis may include features to enhance a flexibility of the endoprosthesis as described in U.S. patent application Ser. No. 11/025,158, and filed concurrently herewith, which application is incorporated herein by reference.

An endoprosthesis may include a deposited thin film and a polymer as described in U.S. patent application Ser. No. 11/025,867, and filed concurrently herewith, which application is incorporated herein by reference.

An endoprosthesis may include one or more filaments, e.g., wires, adapted to enhance mechanical properties of a deposited thin film as described in U.S. patent application Ser. No. 11/025,684, and filed concurrently herewith, which application is incorporated herein by reference.

Methods for loading an endoprosthesis into a delivery device and systems for delivering an endoprosthesis to a treatment site are described in U.S. patent application Ser. No. 11/025,660, which application is incorporated herein by reference.

All publications, references, applications, and patents referred to herein are incorporated by reference in their entirety.

Other embodiments are within the claims.

What is claimed is:

1. An endoprosthesis, comprising:
   a stent comprising a plurality of longitudinal members defining a plurality of first openings, each longitudinal member is in the form of a wire extending along a direction substantially parallel to a longitudinal axis of the stent; and
   a metallic film comprising an alloy comprising nickel, titanium, and chromium, the metallic film having a thickness of about 50 µm or less, covering at least a portion of the stent, and occluding at least a portion of the plurality of first openings
   wherein the film includes a plurality of pores having a size suitable to facilitate adhesion of cells thereto; wherein each pore has a depth of 25 microns or less.

2. The endoprosthesis of claim 1, wherein a ratio of the weight of chromium to a combined weight of nickel, titanium, and chromium is less than 0.0075.

3. The endoprosthesis of claim 2, wherein a ratio of a combined weight of nickel and titanium a weight of the metallic film is at least 0.99.

4. The endoprosthesis of claim 1, wherein the chromium is uniformly distributed throughout the metallic film.

5. The endoprosthesis of claim 1, wherein the metallic film is a nickel, titanium, and chromium alloy.

6. The endoprosthesis of claim 1, wherein the metallic film is a vapor deposited film.

7. The endoprosthesis of claim 1, wherein the metallic film comprises about $5 \times 10^7$ dislocations per $cm^2$ or more.

8. The endoprosthesis of claim 1, wherein the metallic film is attached to the stein.

9. The endoprosthesis of claim 1, wherein the metallic film comprises a plurality of second openings, each of the first openings has a first area, and each of the second openings has a second area smaller than the first area.

10. The endoprosthesis of claim 8, wherein the metallic film is attached to the stent by blazing, welding, or crimping, or the metallic film is attached to the stent by to filament, a rivet, a grommet, or an adhesive.

* * * * *